United States Patent [19]

Hogan

[11] 4,158,777

[45] Jun. 19, 1979

[54] X-RAY APPARATUS

[75] Inventor: William F. Hogan, Westville, N.J.

[73] Assignee: Spectrum X-Ray Corporation, Westville, N.J.

[21] Appl. No.: 865,172

[22] Filed: Dec. 28, 1977

[51] Int. Cl.² .......................................... G03B 41/16
[52] U.S. Cl. ................................ 250/445 R; 250/490
[58] Field of Search ................... 250/490, 444, 445 R, 250/445 T, 446, 447, 448, 449, 451

[56] References Cited

U.S. PATENT DOCUMENTS 4,024,403  5/1977  Bernstein .......................... 250/445 R Primary Examiner—Craig E. Church
Attorney, Agent, or Firm—Paul & Paul

[57] ABSTRACT

An X-ray apparatus includes an image amplifier assembly located above the patient's support table and an X-ray tube located below the patient table. Linkage means couple the image amplifier and X-ray tube such that when the image amplifier is moved, either toward the head end or toward the foot end of the patient table, reaction force components are set up which cause the X-ray tube and its casing to simultaneously shift laterally in a direction opposite to that in which the image amplifier assembly is being moved and to simultaneously pivot angularly on its shifting pivot axis. The extent of the pivotal angular movement corresponds to that of the image amplifier, thereby to maintain the axis of the X-ray beam perpendicular to the image plane of the image amplifier in its shifted angulated position. Lateral shifting of the pivot axis of the X-ray tube and its casing in a direction opposite that in which the image amplifier is being moved, allows a larger portion of the X-ray beam to pass through the fixed opening in the cover of the cabinet which houses the X-ray tube. Lateral shifting and simultaneous pivotal movement of the X-ray tube and its axis is achieved by means of a laterally movable trolley on which the X-ray tube is supported and by a cam and cam-follower arrangement which pivots the tube and its casing in response to lateral movement of the trolley.

5 Claims, 9 Drawing Figures

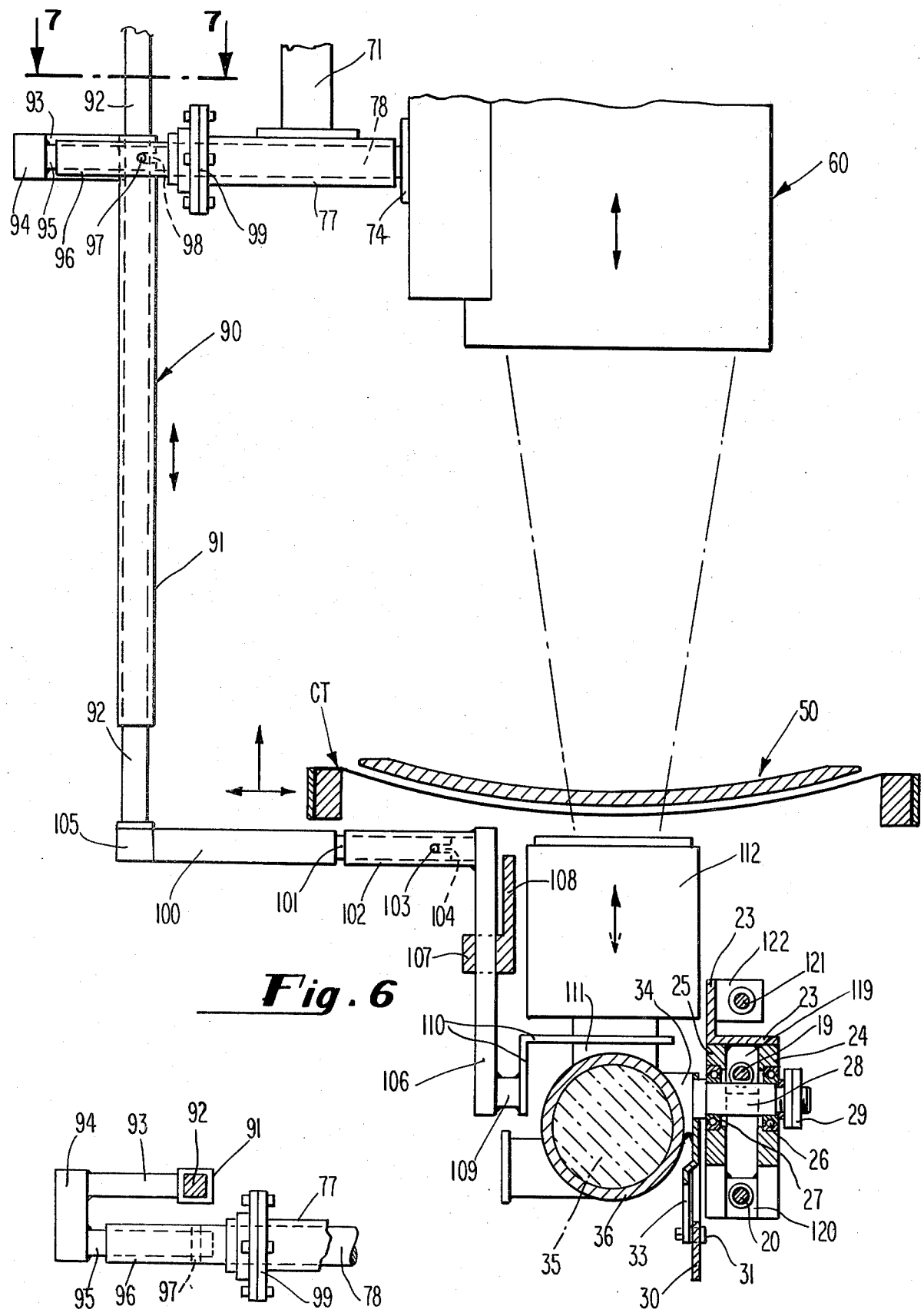

X-RAY APPARATUS

BACKGROUND OF THE INVENTION

This invention relates to X-ray apparatus which is useful for general X-ray diagnostic work but which has the capability of being quickly converted to a form useful for making specialized vascular studies, such as arteriographic studies of the heart.

Prior art apparatus for making general purpose X-ray examination, as well as specialized arteriographic studies of the heart, have included a patient supporting table, an X-ray source on one side of the patient supporting table, and an X-ray imaging system on the other side, with the X-ray source and the imaging system so mounted that the central X-ray beam remains directed at the image plane for various angles at which the heart is to be viewed.

A typical prior art X-ray imaging system includes an electronic image amplifying tube whose function is to convert an X-ray image into a small bright optical image that appears on a phosphorescent disc. Mounted above the disc is a television camera which is used to display the converted X-ray image on a television monitor.

In the present application, the term image amplifier will, for convenience, be used to designate the image amplifier housing and all of its contents, including the image intensifier, the television camera, and any other devices which may be contained in or affiliated with the image intensifier system. In a typical case, the image amplifier is mounted above the cradle and table top on which the patient is supported, with the X-ray tube being located below the patient-supporting cradle and table top.

If the patient to be examined is placed in a horizontal cradle supported on a horizontal table top, the X-ray beam will pass vertically through the patient to the image intensifier, and important blood vessels which are disposed with their axes perpendicular to the viewing plane will be difficult to observe and study. Moreover, certain blood vessels in the heart may be concealed by other blood vessels so that it will be difficult to observe and study them. One solution proposed by the prior art to this problem has been to angulate the X-ray source and the image intensifier jointly. Another proposal by the prior art has been to support the patient in a cradle and on a table which is capable of being rotated and angulated relative to the X-ray beam, thereby to enable viewing of the heart from various angles. In yet other prior art designs, the X-ray source and image intensifier are angulated and the patient is also supported for limited rotational movement.

In some prior art apparatus of the foregoing types, the patient is supported on a table and the X-ray source and the image intensifier are mounted in free space. Such an arrangement is subject to a major disadvantage in that the operator is not shielded from stray and secondary X-ray radiation.

More recently, improved apparatus directed to the foregoing problem has been provided. Such apparatus is disclosed in Bernstein et al U.S. Pat. Nos. 4,024,401 and 4,024,403, each assigned to General Electric Company. Bernstein et al U.S. Pat. No. 4,024,401 discloses a floor mounted enclosure, a patient supporting table on the enclosure, an X-ray tube casing mounted in the enclosure for angulating movement about a fixed axis, an X-ray image-intensifier assembly supported above the table for angulating movement, and an extensible-contractable optionally removable link arm for coupling the X-ray tube casing and the image-intensifier assembly to provide coordinate angulation of the X-ray tube relative to the image-intensifier assembly. It is to be particularly noted that in this prior art U.S. Pat. No. 4,024,401, the X-ray tube casing is angulated on a fixed pivot axis. A disadvantage of such construction is that it imposes an undue restriction upon the extent to which the system can be angulated without having the material surrounding the exit opening in the cabinet cut off an undesirably large part of the X-ray beam.

SUMMARY OF THE INVENTION

A principal object of the present invention is to provide apparatus of the general type disclosed in Bernstein et al U.S. Pat. No. 4,024,401 but incorporating one or more improved features.

A more specific object is to provide improved means for effecting simultaneous and coordinate angulation of the X-ray tube and image amplifier assembly.

An important object is to increase the degree of angulation which may be made without cutting off a significant portion of the X-ray beam.

Another object is to provide apparatus of the above type which is capable of being angulated in either direction to an equal extent.

The foregoing objects, as well as other objects and advantages, are achieved by providing associated trolley means and cam means whereby the X-ray tube casing is caused to shift laterally in an opposite direction while the casing is simultaneously being angulated about a shifting pivot axis.

BRIEF DESCRIPTION OF THE DRAWINGS

FIG. 6 is a side elevational view looking along the lines 6—6 of FIG. 5.

FIG. 7 is a detailed view looking down along the lines 7—7 of FIG. 6.

DETAILED DESCRIPTION OF THE PREFERRED EMBODIMENTS

Figure 1:
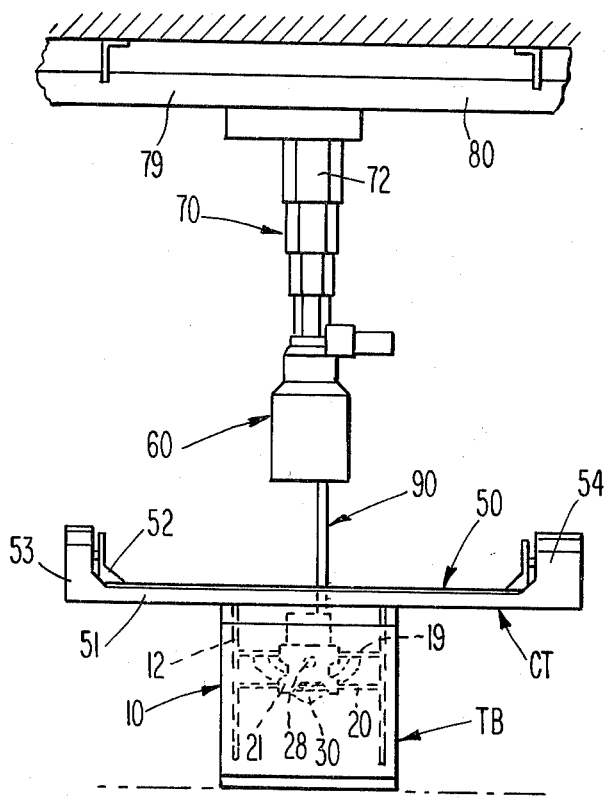
FIG. 1 is a front elevational view of X-ray apparatus incorporating the present invention.
Figure 2:
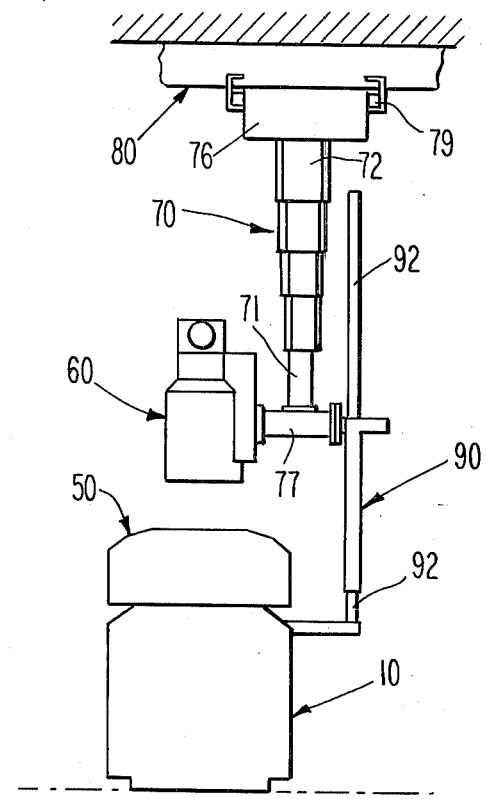
FIG. 2 is a side elevational view of the X-ray apparatus of FIG. 1.

FIGS. 1-4 are overall views of X-ray apparatus embodying the present invention. Structural details are shown in FIGS. 5-8. A table base or pedestal 10 contains an elevator 12 which supports an upper and lower cross rail 19 and 20 on which a trolley 21 is movable. Trolley 21 supports a short horizontal shaft 28 on which an X-ray tube 35 is supported, as by a bracket 34 (FIG. 6). Mounted above the X-ray tube 35 is an image amplifier 60. Image amplifier 60 is supported by a vertical telescoping assembly 70, the lowermost section being identified 71 and the uppermost 72. The telescoping sections are supported in depending position from a fixed member 76 which is mounted for lateral movement in the lengthwise direction of the table top 50 on overhead tracks 79. Tracks 79 are supported from a crane 80 which is movable laterally on tracks in a direction transverse to the longitudinal axis of the table top 50.

Image amplifier 60 and X-ray tube 35 are interconnected by a link arm assembly identified generally by the reference numeral 90. The construction is such that when the image amplifier 60 is moved by the technician from a center position such as is shown in FIG. 1, toward the left or head end 53 of the table top, and in so moving assumes the tilted or angular position illustrated in FIG. 3, the trolley 21 will simultaneously be shifted a few inches toward the right or foot end 54 and the X-ray tube 35 will simultaneously be cammed angularly by cam 30 through that number of degrees which is needed to keep the X-ray beam perpendicular to the image plane of the tilted image amplifier 60.

Figure 4:
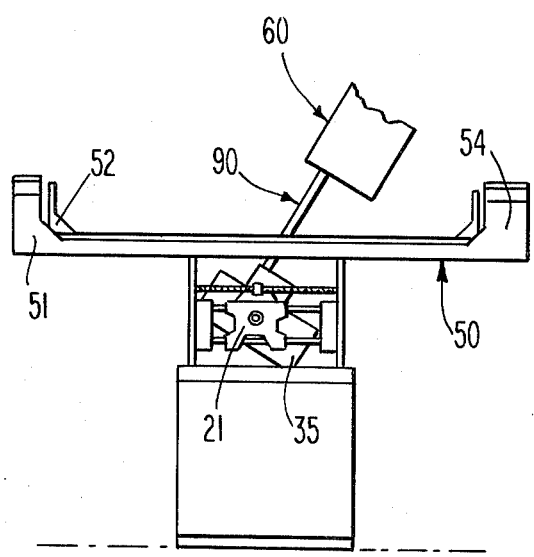
FIG. 4 is generally similar to FIG. 3 but shows the image amplifier moved toward the foot of the table.
Figure 8:
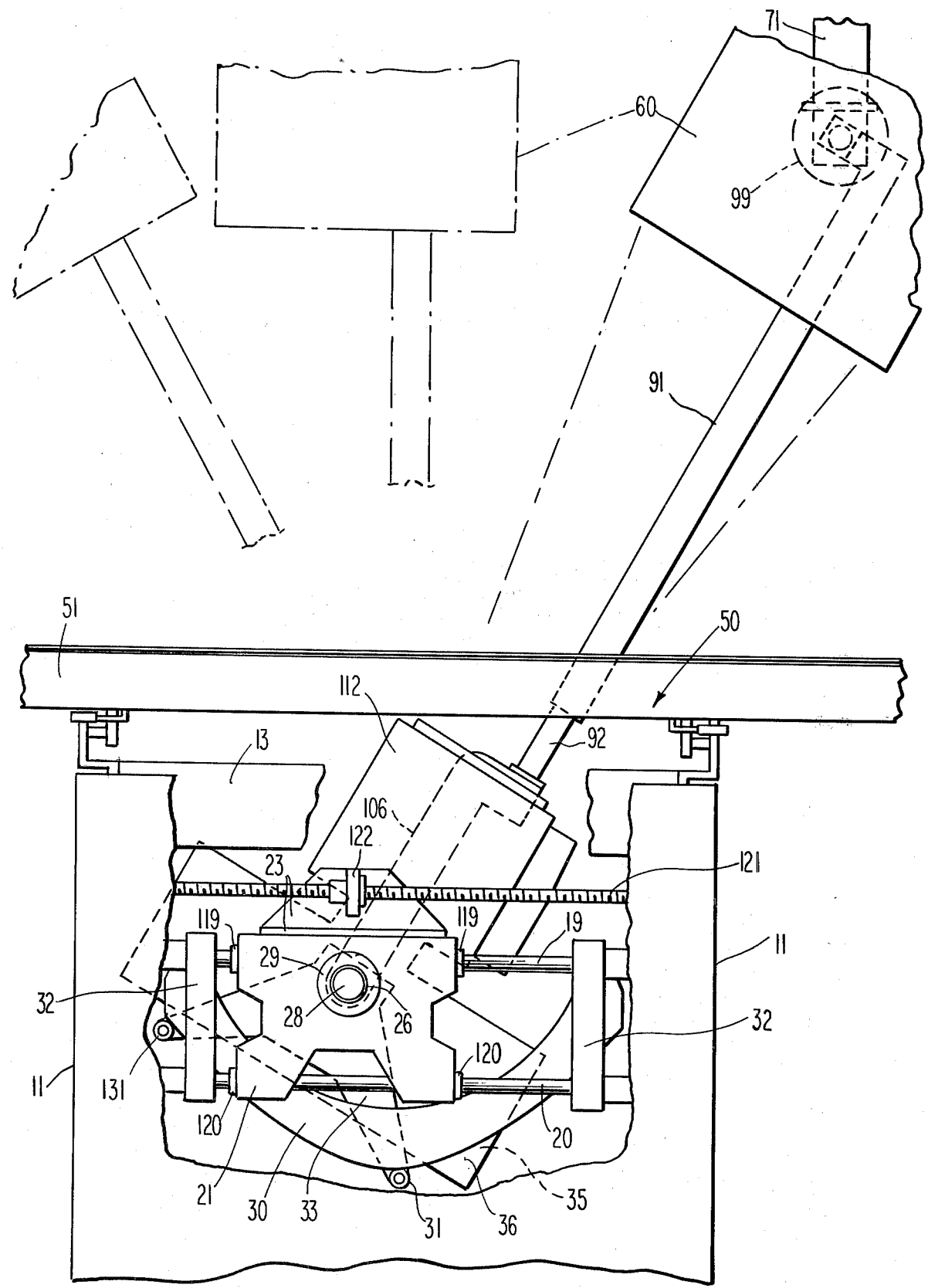
FIG. 8 is an enlarged view generally similar to FIG. 5 but shows the image amplifier shifted toward the foot of the table, as in FIG. 4.

Similarly, when the image amplifier 60 is moved from the center position shown in FIG. 1 toward the right or foot end 54 of the table and in being so moved assumes the angular position indicated in FIG. 4, the trolley 21 will be shifted simultaneously a few inches toward the left or head end of table top 50 and the X-ray tube 35 will simultaneously be moved angularly to the position indicated in FIGS. 4 and 8 such that the beam projected by the X-ray tube remains perpendicular to the image plane of image amplifier 60 which has now assumed the angular position indicated in FIGS. 4 and 8.

Although not visible in the drawings, it will be understood that the elevator 12 is a cabinet having a steel cover to inhibit radiation of X-rays from the X-ray tube. An opening is, of course, provided in the cover to allow for passage of the X-ray beam from the X-ray tube up through the X-ray transmissive table and cradle, through the patient, and onto the image plate of the image amplifier 60. The opening in the cover of the elevator cabinet 12 is made large enough to pass the beam, but is otherwise kept as small as possible to avoid unnecessary radiation. It will be understood that when the technician moves the image amplifier 60 toward the head end 53 of the table top as in FIG. 3, or toward the foot end as in FIG. 4, the X-ray beam tends to be partially cut off by the edge of the opening in the cabinet cover. The apparatus of the present application is designed to avoid or reduce such partial cut off of the beam by the elevator cover.

Figure 3:
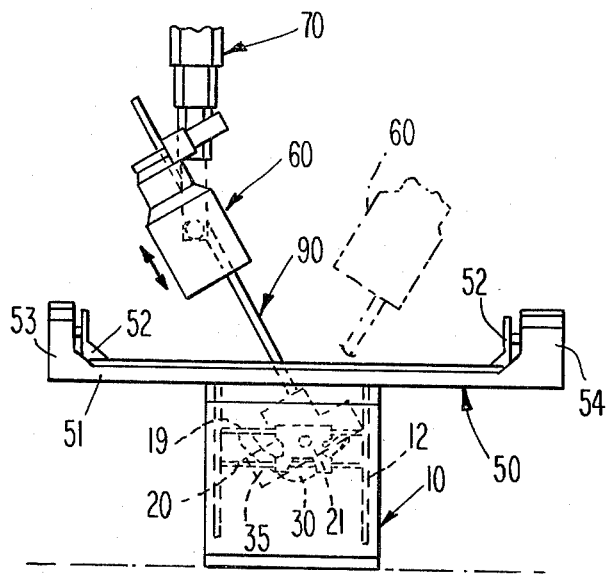
FIG. 3 is generally similar to FIG. 1 but shows the image amplifier moved toward the head of the X-ray table.

In prior art apparatus of the type now being described, when the image amplifier 60 is moved from a central position toward the head end, or toward the foot end, of the table, the X-ray tube is simultaneously pivoted on a fixed axis. In contrast to such prior art apparatus, in the apparatus of the present application, when the image amplifier 60 is moved toward the head end or toward the foot end of the table, the X-ray tube 35 is simultaneously pivoted on a pivotal axis which simultaneously shifts laterally, toward the left or toward the right, in whatever direction is opposite to that in which the image amplifier is being moved. For example, when the technician moves the image amplifier 60 toward the left or head end 53 of the table, counterclockwise as illustrated in FIG. 3, the X-ray tube 35 is simultaneously pivoted counterclockwise on a pivot axis which simultaneously shifts to the right or foot end of the table. Conversely, when the technician moves the image amplifier 60 toward the foot end 54 of the table, as illustrated in FIG. 4, the X-ray tube 35 is simultaneously pivoted on a pivot axis which simultaneously shifts toward the head end 53 of the table. Such simultaneous shifting of the pivot axis in the opposite direction has an important advantage. It avoids, or at least reduces, partial cutting off of the X-ray beam at the cover opening. The mechanism by which simultaneous shifting of the X-ray tube pivot axis is accomplished will now be described.

Figure 5:
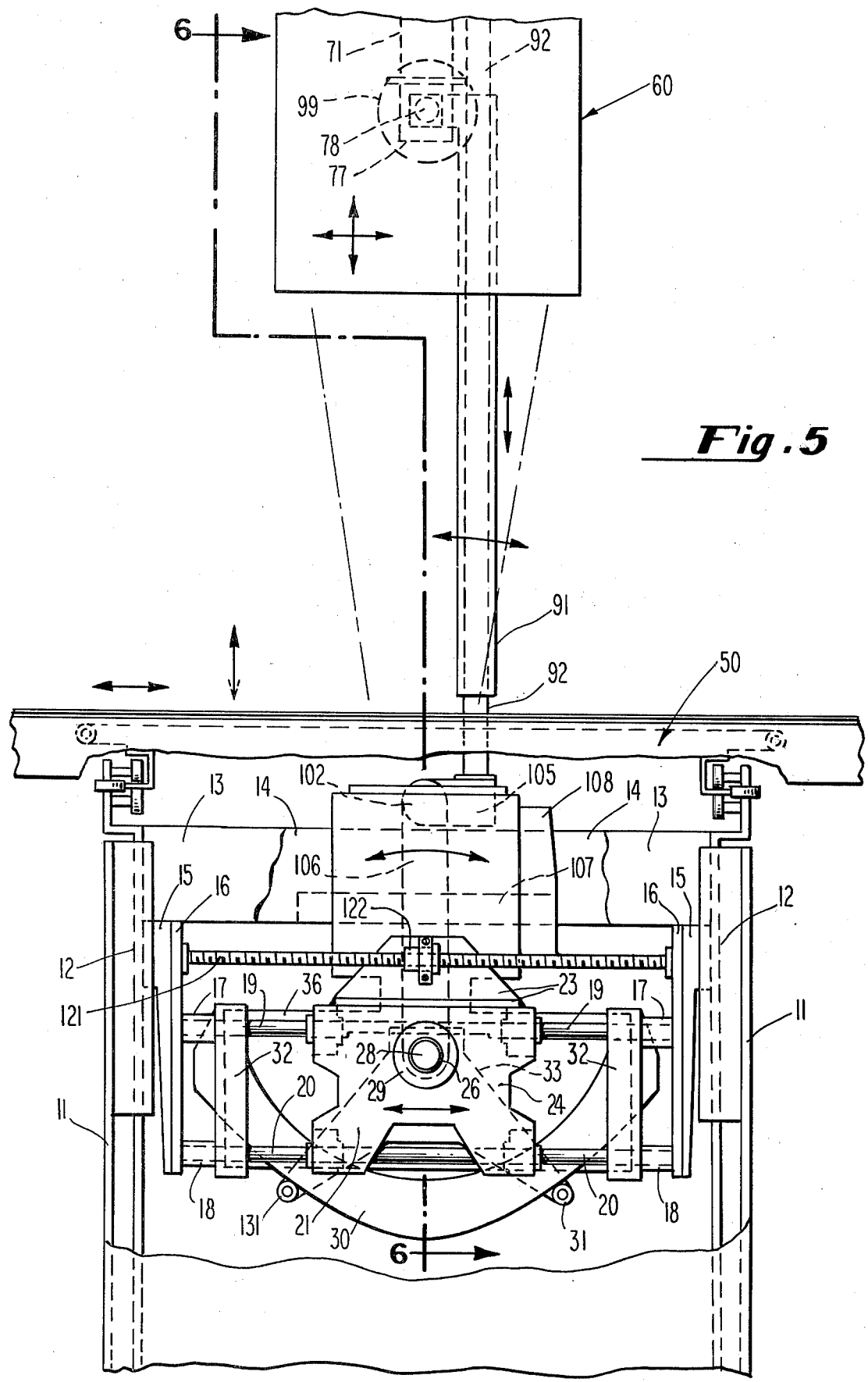
FIG. 5 is an englarged front elevational view showing details of the apparatus of the present application.

Referring now to FIGS. 5–7, the X-ray tube 35 and its casing 36 are supported as by bracket 34 (FIG. 6) which is fixed to and supported by a short shaft 28 which is supported for angular movement in a pair of bearings 26, 27, which in turn are supported in trolley 21. Trolley 21 comprises side plates 24 and 25 spaced apart and having therebetween a pair of upper bushings 119 and a pair of lower bushings 120. An upper rail 19 passes through bushings 119, and a lower rail 20 passes through bushings 120. Rails 19 and 20 are supported in a pair of side plates 16 which are attached to side frame members 15 of the elevator 12. Trolley 21 is slidable on the rails 19 and 20.

Mounted on rails 19 and 20 as by a pair of brackets 32 is an arcuate cam 30, best seen in FIG. 5. A bifurcated plate member 33 is supported on shaft 28. Plate member 33 carries, at each end of its two legs, a cam-follower roller 31 and 131. These cam-follower rollers 31 and 131 engage the lower edge of the cam 30.

Referring again to FIG. 6, secured to casing 36 of X-ray tube 35 is an angle bracket 110 which is connected, as by connecting member 109 to a vertically extending bar 106 which passes through a retaining slot in a guide member 107. The slot is elongated to allow for pivotal movement of bar 106 within the guide member 107. Extending rearwardly from the top end of vertical bar 106 is a tubular member 102 which receives the cylindrical forward portion 101 of a link member 100. The cylindrical portion 101 has a clevis 104 at its forward end which receives a transverse pin 103 to prevent angular movement of 101 relative to 102. At the rearward end of member 100 is a short lateral member 105 (FIG. 5) and extending upwardly from the end of member 105 is a vertical bar 92 of square cross-section, which is received within a square tubular member 91. The vertical bar 92 extends well beyond the upper end of tubular member 91. As seen best in FIG. 7, secured to the upper end of the tubular member 91 is a short rearwardly-extending member 93 which is secured to a short cross member 94 which supports a forwardly-extending member 95 which is received within a tubular member 96. A clevis pin 97, received within a clevis 98, prevents rotation of 95 relative to 96. Extending forwardly from the tubular member 96, and connected thereto by a bearing housing 99, is a tubular member 77 which receives a cylindrical member 78, which is connected, as by bracket 74, to image amplifier 60.

All of the linkage mechanism just described above is identified generally by the reference numeral 90 and is referred to as the linkarm assembly. The function of the linkarm assembly is to assure simultaneous angulation of the X-ray tube 35 when the image amplifier 60 is moved from its center position toward either the head end or foot end of the X-ray table. It will be seen from FIGS. 1–4 that when the image amplifier 60 is moved toward the head end 53, or toward the foot end 54, of the X-ray table, the image amplifier 60 takes on an angular position relative to the horizontal. The function of the linkarm assembly 90, as just described, is to assure that the X-ray tube 35, located below the patient table 50, is angulated simultaneously to an extent corresponding to that of the angulation of the image amplifier 60, located above the patient table, to assure that the beam of the X-ray tube remains perpendicular to the image plane of the image amplifier.

Referring again to FIGS. 5–7, to move the image amplifier 60 in the lengthwise direction of the X-ray table, for example, toward the foot end 54 of the table, as illustrated in FIGS. 4 and 8, the technician may push or pull on the upper portion of bar 92. The image amplifier 60 is connected to bar 92 by way of bracket 74, rearwardly extending arm 78, tubular member 77, bearing housing 99, tubular member 96, member 95, end member 94, forwardly extending member 93 and tubular member 91. When the vertically extending rod 92 is moved, the following members are also moved, 105, 100, 101, 102, 106, 109, 110, 111, and casing 36 of the X-ray tube.

When the image amplifier 60 and the linkarm assembly 90 is pulled or pushed by the technician toward the foot of the table, which is to the right as viewed in FIG. 5, to take up the position illustrated in solid line in FIG. 8, the X-ray tube 35 and its casing 36 are urged to pivot clockwise on shaft 28. Pivot shaft 28, however, is not fixed against lateral movement since it is carried on trolley 21 which is able to move laterally to a limited extent. Thus, when the image amplifier 60 and upper bar 92 are pushed or pulled to the right to cause X-ray tube 35 to pivot clockwise on shaft 28, the reaction force causes shaft 28 and trolley 21 to move laterally to the left. When this happens, cam follower rollers 31 and 131, carried by plate 33 and supported on shaft 28, are caused to move from the positions shown in FIG. 5 to the position shown in FIG. 8. In so moving, the rollers 31 and 131 follow the contour of cam 30. Thus, the angular movement of the X-ray tube 35 is controlled by the contour of cam 30. In some cases, relative angular movement between the image amplifier 60 and the X-ray tube may be necessary, and such relative motion is provided for by members 77 and 78. Cylindrical member 78 is fixed to image amplifier 60 but is movable angularly within tubular member 77.

It is to be particularly noted that, unlike such prior art X-ray apparatus as is shown in U.S. Pat. No. 4,024,401, the X-ray tube does not pivot on a fixed pivot axis in response to shifting of the image amplifier.

If, instead of pulling or pushing on the upper portion of the bar 92, or on the image amplifier itself, the technician pulls or pushes on the lower portion of bar 92 (FIG. 5) a lateral force component will be imposed on the X-ray tube casing 36 and on shaft 28 and on trolley 21, but trolley 21 will not be able to move laterally in either direction, without causing pivotal movement of casing 36. This pivotal movement is, of course, caused by the cam-follower rollers 31 and 131 which bear against the lower edge of cam plate 30. In response to a pull or push on the lower part of bar 92, trolley 21 will move laterally to a limited extent but its lateral movement will be in a direction opposite to that of the lateral force applied to bar 92. Of course, if a lateral force is applied directly to the trolley 21, the trolley will move laterally in the same direction but the image amplifier 60 and the linkarm assembly 90 will pivot in the opposite direction. For example, if the technician pushes on trolley 21 in a direction to move the trolley to the right, as viewed in FIG. 5, the image amplifier 60 and the linkarm assembly 90 will move pivotally in a counterclockwise direction.

Figure 9:
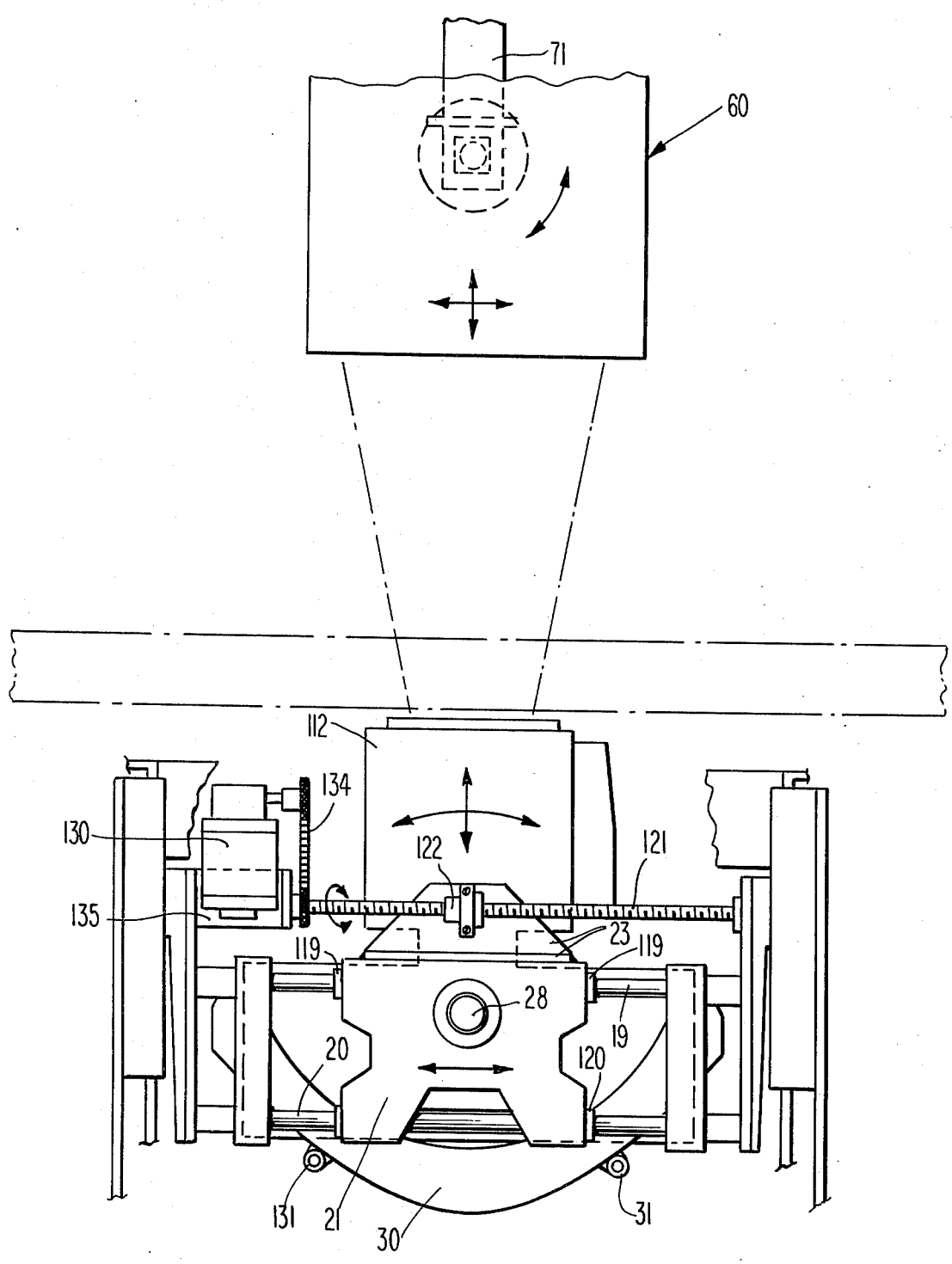
FIG. 9 is generally similar to FIG. 5 but shows a motor drive for the screw.

FIG. 9 depicts a motor drive for the trolley 21. Details of the motor drive will be described and claimed in a separate patent application to be filed during the pendency of the present application. It will be sufficient to state here that in response to signals received from a separate motor drive used for positioning the image amplifier 60, the motor 130 shown mounted on bracket 131 will by means of sprocket-and-chain 134, drive an elongated screw 121 mounted above and parallel to the upper trolley rail 19. A ball nut 122 on the screw 121 is fastened to the upper portion of angle plate 23. The lower portion of plate 23 is connected to trolley 21. This is best seen in FIG. 6. Hence, when screw 21 is rotated, in one direction or the other, the ball nut 121 moves laterally carrying with it angle plate 23 and trolley 21. Lateral movement of trolley 21 causes angular movement of X-ray tube 35 and its casing 36 due to the action of cam 30 and cam-follower rollers 31 and 131, as has already been described. The ball nut 122 damps out any tendency of the trolley to continue movement after motor 130 has been shut off.

It will have been noted that the elongated screw 121 and the ball nut 122 are also provided in the manual drive form of X-ray apparatus shown and described in the present application. The function, however, of screw 121 and ball nut 122 in the manual form of apparatus is different. In the manual form of apparatus the ball nut 122 functions as a safety device. For example, if the linkarm assembly 90 were to be disconnected at its upper end, i.e. at the image amplifier end, and if the technician failed to hold on to the linkarm assembly, the weight of the linkarm assembly would cause it to fall pivotally toward the floor. This would shock and possibly damage the X-ray tube. To avoid such occurrence, the ball nut 122 functions to dampen and restrain rapid movement of trolley 21. In effect, the ball nut 122 absorbs the shock which would otherwise be imposed on the X-ray tube.

Several of the reference numerals appearing in the drawings have not yet been identified. Reference numeral 112 (FIGS. 6,8,9) identifies the collimator for the X-ray beam. Reference numeral 52 (FIGS. 1–4) identifies the cradle which is supported in cradle top CT for rotation about is longitudinal axis. Reference numeral TB (FIG. 1) identifies the table base, comprising the pedestal cabinet 10 and the elevator 12. Reference numerals 17 and 18 (FIG. 5) identify the hollow bosses which support the trolley rails 19 and 20. Reference numerals 13,14 (FIGS. 5,8) identify the front and back cross beams of the elevator 12.

Having described the X-ray apparatus of the present invention, its advantages will be summarized. In the prior art appartus, such as in U.S. Pat. No. 4,024,401, the X-ray tube and its casing are pivoted about a fixed axis. The X-ray tube and its fixed axis are, of course, located within a cabinet or housing of some sort, and such cabinet or housing necessarily has an exit opening in its cover or top plate to allow for passage of the X-ray beam up through the patient and on to the image plane of the image amplifier. Ordinarily, the focal and pivot axis of the X-ray tube would be in the vertical plane of the center axis of the exit opening, and angulation of the beam, either toward the head or foot of the patient, is limited by the size of the exit opening. It is, of course, desirable to keep the exit opening as small as possible in order to avoid undue and unwanted radiation. If angulation of the X-ray beam is unduly limited, examination of the heart of the patient can be carried out only by moving the patient, not only rotationally but also longitudinally.

Less patient movement, particularly longitudinal movement, is required if the X-ray beam can be angulated to a greater extent without being cut off by the top plate material surrounding the exit opening. Such increase in angulation is achieved by the apparatus of the present application. This is achieved by moving the focal pivot axis of the X-ray tube laterally in a direction opposite to that in which the examination of the patient is to be made. For example, if the X-ray beam axis when vertically oriented would pass through the midsection of the patient, and if the heart of the patient is to be examined, then when the image amplifier is moved laterally from the midsection toward the heart section, the focal axis of the X-ray tube is simultaneously moved toward the foot of the patient, and simultaneously the X-ray tube is also pivoted by the cam assembly to an extent corresponding to the angulation of the image plane of the image amplifier. In this way, the axis of the beam is maintained perpendicular to the now angulated plane of the image amplifier, with most of the beam being able to pass through the exit opening.

In a typical case, two inches of movement laterally by trolley 21, in either direction, will provide 30° of angulation, in the opposite direction.

The foregoing description has assumed that the X-ray tube is symmetrical about its focal point which is located on the pivot axis. If the X-ray tube is not symmetrical, the cam rail 30 can be contoured to provide different angular movement of the X-ray tube for so-many degrees of movement of the trolley on the cam rail.

The X-ray apparatus described will probably be used for coronary arteriographic examination about 10° of the time, and used for general X-ray examination about 90° of the time. The link arm assembly shown and described would interfere with general examination studies and is designed, therefore, for quick assembly and disassembly. Special lock means may be employed to prevent disassembly except when the image amplifier and X-ray tube are in vertical alignment. Such special lock means have broader application and will be described in a separate application.

What is claimed is:

1. A X-ray examination system which includes among its components an X-ray source, an image amplifier, and a patient supporting table positioned between the X-ray source and the image amplifier, the arrangement being such that the axis of the X-ray beam is perpendicular to the plane of the image amplifier;
   a. means for mounting the image amplifier for pivotal movement about an axis which is movable in a direction having a component lateral to the axis of the X-ray beam;
   b. means for mounting the X-ray source for pivotal movement about an axis which is movable in a direction having a component lateral to the axis of the X-ray beam; and
   c. means for interconnecting the image amplifier and X-ray source such that, in response to lateral and angular movement of the image amplifier on its axis, the X-ray source is simultaneously moved angularly and laterally, the angular movement corresponding to the angular movement of the image amplifier, and the component of lateral movement being in a direction opposite to the component of lateral movement of the image amplifier.

2. Apparatus according to claim 1 wherein said means for mounting said X-ray source includes:
   a. horizontal rail means;
   b. a trolley mounted for lateral movement on said rail means;
   c. a support shaft connecting said trolley and said X-ray source;
   d. cam means supported on said rail means;
   e. cam follower means supported on said support shaft and movable therewith, lateral movement of said trolley causing angular movement of said X-ray source on said support shaft.

3. Apparatus according to claim 2 wherein said means for interconnecting the image amplifier and X-ray source comprises mechanical linkage means.

4. X-ray apparatus for conducting general X-ray body examination and also coronary arteriographic examinations, said apparatus comprising:
   a. overhead carriage means movable in lateral directions;
   b. extensible and contractible telescoping support means;
   c. an image amplifier system;
   d. a first pivot shaft for supporting said image amplifier system at the lower end of said telescoping means for angular movement of said image amplifier system;
   e. an X-ray source disposed below said image amplifier system and spaced therefrom for accommodating an examination subject therebetween;
   f. trolley means;
   g. trolley rail means for supporting said trolley means for lateral movement;
   h. a second pivot shaft carried by said trolley means;
   i. means supporting said X-ray source on said second pivot shaft such that its focal point is on the axis of said pivot shaft, the axis of said second pivot shaft being parallel to that of said first pivot shaft;
   j. extensible and contractible link arm means having its upper end connected to said image amplifier system and its lower end connected to said X-ray source; and
   k. cam means supported on said second pivot shaft for causing angular movement of said X-ray source in response to lateral movement of said trolley means the arrangement being such that in response to lateral and angular movement of the image amplifier on its shaft, the x-ray source is simultaneously moved laterally and angularly, the angular movement corresponding to the angular movement of the image amplifier and the component of lateral movement being in a direction opposite to the component of lateral movement of the image amplifier so that the axis of an x-ray beam from the source remains perpendicular to the input plane of the image amplifier.

5. X-ray apparatus according to claim 4 wherein:
   a. said X-ray source comprises an X-ray tube having a focal point and an X-ray tube casing;
   b. said lower end of said link arm means is connected to said X-ray tube casing;
   c. said second pivot shaft is connected to said X-ray tube casing, the constructional arrangement being such that a lateral force applied to said link arm means in one direction causes said trolley means to move laterally in the opposite direction as a result of a reaction force created by said cam means, said cam means opposing movement of said trolley means in the same direction as that of the lateral force applied to said link arm means and causing said X-ray tube casing to move pivotally about its focal point and also laterally in said opposite direction.

* * * * *